US008967168B1

(12) United States Patent
Gusanders

(10) Patent No.: US 8,967,168 B1
(45) Date of Patent: Mar. 3, 2015

(54) SINK INSERT FOR CLEANING A MEDICAL OR SURGICAL DEVICE

(75) Inventor: Daniel Leonard Gusanders, Glen Ellyn, IL (US)

(73) Assignee: Pure Processing LLC, Carol Stream, IL (US)

( * ) Notice: Subject to any disclaimer, the term of this patent is extended or adjusted under 35 U.S.C. 154(b) by 747 days.

(21) Appl. No.: 13/199,723

(22) Filed: Sep. 7, 2011

Related U.S. Application Data

(60) Provisional application No. 61/402,949, filed on Sep. 8, 2010.

(51) Int. Cl.
*B08B 3/04* (2006.01)
*A61L 2/18* (2006.01)
*A61B 1/12* (2006.01)

(52) U.S. Cl.
CPC ... *B08B 3/04* (2013.01); *A61L 2/18* (2013.01); *A61B 1/121* (2013.01); *A61B 1/123* (2013.01); *A61B 1/125* (2013.01)
USPC .............................................. 134/184; 4/619

(58) Field of Classification Search
CPC ........ A61B 1/121; A61B 1/123; A61B 1/125; B08B 3/04
USPC .............................................. 134/184; 4/619
See application file for complete search history.

(56) References Cited

U.S. PATENT DOCUMENTS

| 2,687,136 | A | * | 8/1954 | Moore ............................. 134/49 |
| 2,765,475 | A | | 10/1956 | Nolan |
| 2,812,518 | A | | 11/1957 | O'Brien et al. |
| 4,336,620 | A | | 6/1982 | Gresh |
| 4,881,281 | A | | 11/1989 | Lavoine et al. |
| 5,361,429 | A | | 11/1994 | Lin |
| 6,494,222 | B1 | | 12/2002 | Mitsumori et al. |
| 6,496,987 | B1 | * | 12/2002 | Chou ............................. 4/227.2 |
| 6,609,258 | B1 | | 8/2003 | Clements |
| 2002/0185165 | A1 | | 12/2002 | Lee et al. |
| 2004/0003460 | A1 | | 1/2004 | Zolotnik |
| 2007/0071832 | A1 | | 3/2007 | Kral et al. |
| 2008/0142049 | A1 | * | 6/2008 | Onishi et al. ............... 134/22.11 |
| 2008/0283095 | A1 | | 11/2008 | Suzuki et al. |

* cited by examiner

*Primary Examiner* — Michael Barr
*Assistant Examiner* — Spencer Bell
(74) *Attorney, Agent, or Firm* — Taft Stettinius & Hollister LLP

(57) ABSTRACT

A sink insert for cleaning a medical device having a lumen, such as an endoscope, includes a basin and a pump connected to the basin. The basin is shaped to fit into a sink, and has lip portions on its side walls shaped to extend outwardly to overlap side walls of the sink. The basin includes a drain formed in its floor; an additive reservoir integrally formed as a depression in its floor; additive fill lines defining pre-calibrated volume measurement areas for measurement of additives in the reservoir; a thermometer; and basin fill lines on its side walls defining pre-calibrated volume measurement areas for measurement of cleaning liquid filled into the basin. The pump includes inlet and outlet tubes for drawing cleaning liquid from the basin into the pump, and for pressurized output of the cleaning liquid from the pump to the medical device.

27 Claims, 8 Drawing Sheets

US 8,967,168 B1

SINK INSERT FOR CLEANING A MEDICAL OR SURGICAL DEVICE

This application claims the benefit of U.S. Provisional Application No. 61/402,949, filed Sep. 8, 2010. The contents of said U.S. Provisional Application No. 61/402,949, filed Sep. 8, 2010, are incorporated herein by reference in their entirety.

BACKGROUND OF THE INVENTION

1. Field of the Invention

This invention is a sink insert that relates to the field of cleaning reusable medical/surgical devices, in particular cleaning devices for soaking and flushing tubular items such as endoscopes.

Current facilities and devices for such cleaning tasks have problems arising from the lack of ease of use and convenience, variability in the effectiveness of the cleansing process, waste of expensive additives and supplies, and/or ergonomic problems for the technician cleaning the devices. Historically, the lumens of tubular medical surgical devices have been cleaned by flushing them with treated water using a syringe. The typical method uses water treated with liquid additives or granulated or powdered solid additives, such as various chemicals, solvents, detergents or antibacterial agents needed to properly clean the device. The syringe method entails a laborious process of mixing the additives with the water in a separate container to yield the desired cleaning liquid containing the correct concentration of additives, and then filling the syringe with this cleaning liquid numerous times as well as flushing the syringe numerous times. Among the challenges associated with this process are the various size syringes available to the technician which can be as small as 10 cc-90 cc. Many device manufacturers have pre-cleaning requirements that call for copiously flushing the lumen of the device. Copious flushing with a small syringe is labor intensive and physically challenging, involving time consuming repetitive motion, and possible waste of expensive additives.

This sort of syringe flushing task is often performed in a deep laboratory sink. Deep sinks are often the enemy of the technician because of intensive bending needed to reach the sink bottom. Sinks in medical or hospital facilities are often designed to be large and deep so that they can accommodate the largest items intended to be cleaned in them. However, smaller items also must be cleaned in that sink, resulting the need for the technician to bend over, causing backaches, fatigue, and ergonomic problems. Deep sink platforms do not allow the technician to have the surface of the cleaning liquid at the optimal working height unless there is tremendous amount of cleaning liquid in the sink, and the bottom working surface of such a sink is often too low to provide an optimal working height.

In the field of cleaning medical/surgical devices, the concentration of an additive in the cleaning liquid is very important to the proper cleaning of the device. Historically methods used to dilute hospital grade chemicals in open sinks have been done via educated guess. Sinks are not marked with measuring lines and chemicals used have to be diluted properly to be effective. Medical technicians are left to improvise either by estimating, painting lines, etching lines or fastening stickers that indicate line volume in the sink basin. Though there are many ways to measure chemicals, the most common are with manual pumps that may be provided by the manufacturer of the additive or affixed to its container, or with automated proportioning systems that attach to a sink faucet. While these options are available they are have problems in that, often, manual pumps are ordered separately and automated pumps are not reliable. Many technicians resort to the expedient of simply dumping the additives into the water, with the attendant risks of under- or over-diluting the additives. Measuring cups are often poorly calibrated or subject to user error in over- or under-filling. Use of measuring cups yields its own problems in that the technician has yet another separate item that he must keep track of and must properly clean out after using.

There are many risks associated with under- or over-diluting the additives. Some chemicals used in certain clinical and scientific settings are expensive and caustic. Residue builds up on devices, which can compromise effective clinical and scientific outcomes. Devices with residue often have to be sent out for repair, because the residue could permanently affix during the next stage of processing such as decontamination or sterilization. Ineffective cleansing can occur if an inadequate amount of a chemical is dispensed for a cleaning task. Proper dilution of additives used in a cleaning task is very important to efficient, economical cleaning and good cleaning results.

2. Description of the Related Art

Prior art devices exist for cleaning of medical and surgical devices. US Patent App. No. US 2008/0283095 discloses an endoscope washer. The device is not a sink insert; it is a separate rolling unit with a complicated and expensive design. U.S. Pat. No. 6,494,222 discloses an ultrasonic cleaning apparatus which is not a sink insert; it is a separate rolling unit with a complicated and expensive design.

US Patent Appl. Pub. No. 2004/0003460 discloses a basin for soaking feet and a disposable liner for the basin.

U.S. Pat. No. 6,609,258 discloses a stand alone automotive and industrial parts washer with a disposable liner and legs for standing on the floor or on a work bench.

U.S. Pat. No. 5,361,429 shows a double tub bath for bathing infants, wherein the secondary tub is supported for vertical adjustment.

U.S. Pat. No. 2,765,475 discloses an adjustable support platform for an infant bathtub adapted to be connected to the wall of a conventional bathtub.

U.S. Pat. No. 4,336,620 shows a self-skimming dish rinser having dimensions small enough to fit within a sink to allow spillover water to reach the drain opening of the sink.

U.S. Pat. No. 4,881,281 shows an infant bathtub having an adjustable inner platform for holding a baby during bathing.

US Patent Appl. Pub. No. US 2002/0185165 shows a complicated medical instrument washer, much like a conventional automatic dishwasher, with spray outlets and racks.

US Patent Appl. Pub. No. 2007/0071832 discloses a method for cleaning a lumen of a medical instrument by injecting a stream of carrier gas and particles, such as dry ice particles, into the lumen.

U.S. Pat. No. 2,812,518 shows a shower spray for bathing infants or feet, to be suspended by a support bracket or to be self-supporting on legs.

BRIEF SUMMARY OF THE INVENTION

The inventor has developed the instant modular sink insert that provides an economical, one-piece, drop-in unit that solves the problems encountered with prior art sinks and apparatus for the cleaning of reusable medical/surgical devices, in particular tubular items such as endoscopes. The inventor's sink insert is integrally formed with a basin and an electrically powered pump having an inlet tube to draw treated water from the basin and to forcibly eject the cleaning liquid through an outlet tube into the lumen of the tubular medical device. The basin includes a calibrated measurement system using a pre-calibrated additive measurement reservoir with additive measurement fill lines and basin measurement fill lines that allow instant and accurate dilution of additives needed for cleaning and disinfection of medical/surgical devices. An integral thermometer allows instant temperature reading to assure that cleaning occurs at the temperatures specified for cleaning the medical/surgical devices and for appropriate use of additives in accordance with label specifications. The insert's basin width, depth, handles, and lip formations are designed to provide an economical and convenient modular unit that fits standard medical laboratory sinks and also is portable, while providing ideal ergonomic features for users.

Figure 1:
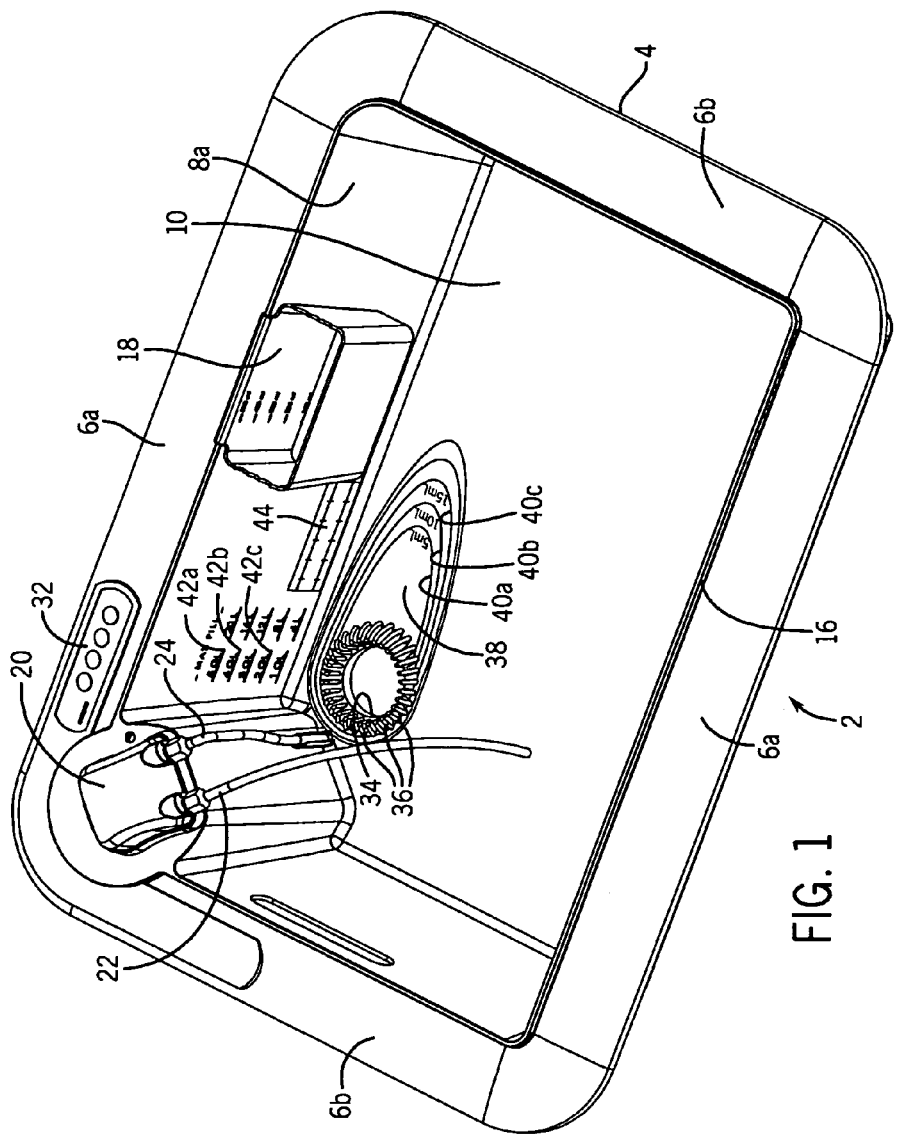
FIG. 1 is a top perspective view of the sink insert of the present invention.

REFERENCE NUMERALS 2 sink insert
4 basin
6a, 6b basin lip formations
8a, 8b basin side walls
10 basin floor
12, 12 basin cutouts
14, 14 basin handles
16 rail
18 caddy
18a caddy perforation
18b caddy fill lines
20 pump
22 pump inlet tube
24 pump outlet tube
26 pump receptacle
28 pump motor
30 pump power supply
32 pump control panel
34 drain
36, 36, 36 catch system protrusions
38 additive reservoir
40a, 40b, 40c additive fill lines
42a, 42b, 42c basin fill lines
44 liquid crystal thermometer strip
100 tubular device to be cleaned
200 sink

DETAILED DESCRIPTION OF THE INVENTION

Figure 7:
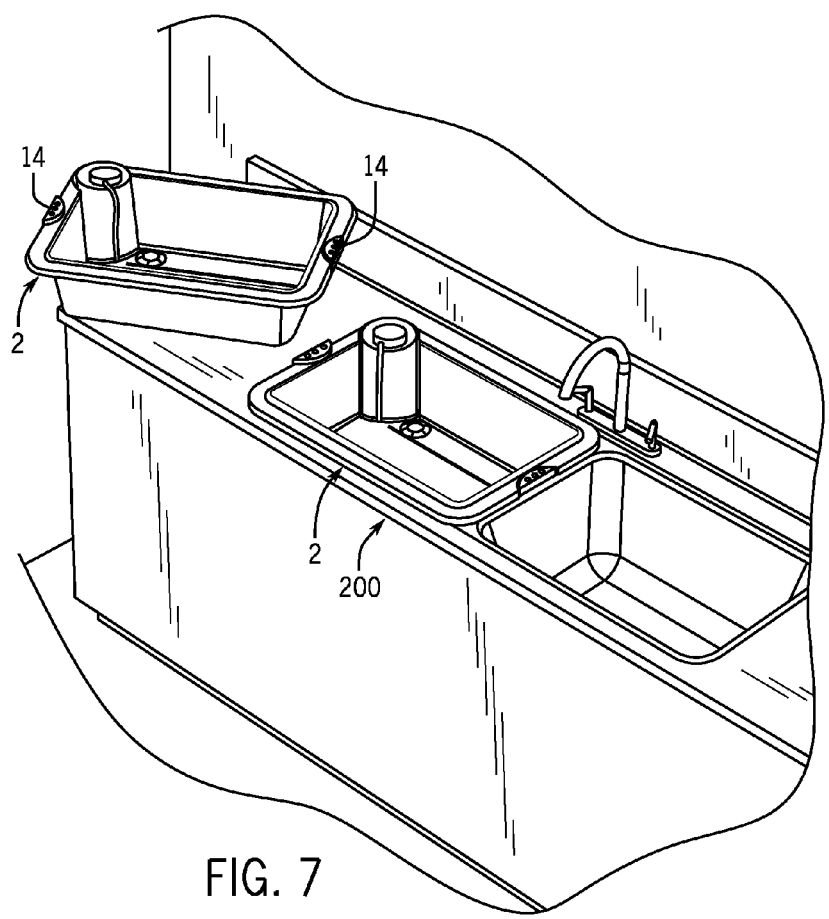
FIG. 7 is a front perspective view showing two of the sink inserts in states of use.

As shown in FIG. 1, the sink insert 2 of the present invention includes a receptacle portion in the form of a basin 4 for holding liquid to be used to clean medical/surgical devices 100 that have lumens. The cleaning liquid typically is water, but alternatively, isopropyl alcohol and/or other alcohols or properly diluted enzymatic solutions or any other compatible solvent cleaning chemicals are used as the cleaning liquid. The sink insert 2 is shaped and adapted to fit into standard sized medical and laboratory sinks 200 (partially shown in FIG. 7). The sink insert 2 also is shaped and configured for the transportation, disassembly, soaking, scrubbing, and/or repairing the medical devices 100 outside of the sink 200. The basin 4 has a plurality of side walls 8a, 8b extending upwardly from a basin floor 10. Typically the basin 4 will have four side walls 8a, 8b forming a roughly square or rectangular shape in a cross-section of the insert 2, but the basin also could have any other appropriate shape for the intended usage, such as having one curved continuous side wall 8a forming a circular or oval cross-sectional shape.

Figure 3:
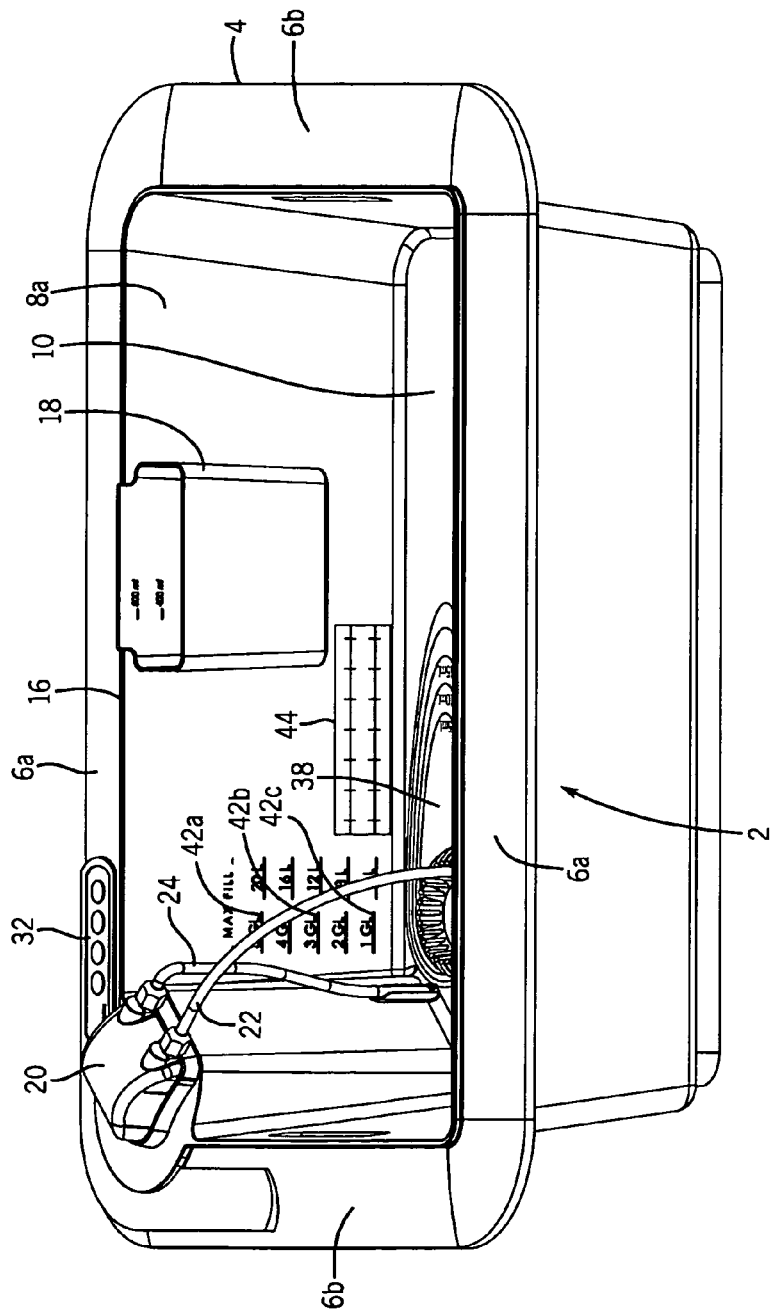
FIG. 3 is a front perspective view of the sink insert.
Figure 4:
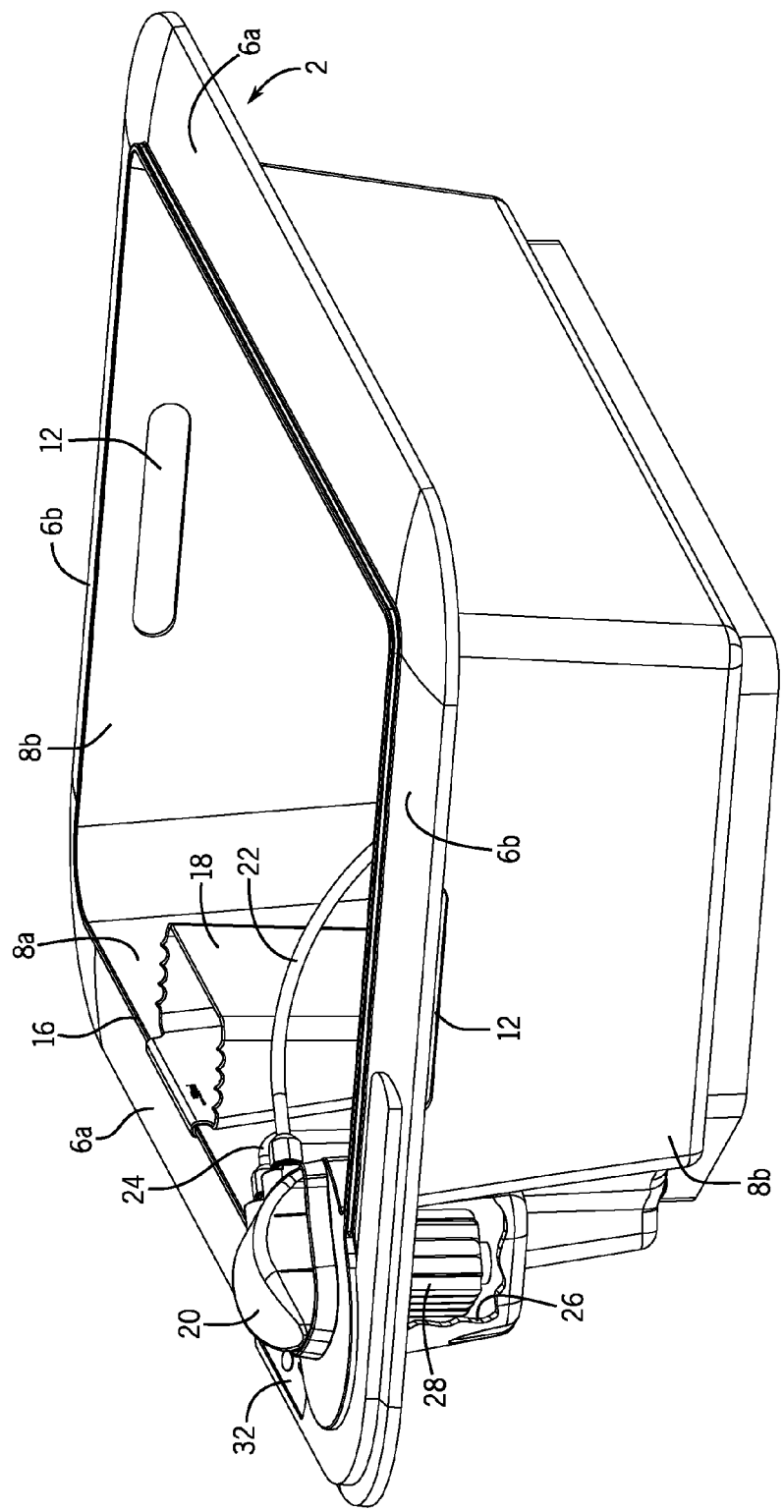
FIG. 4 is a left side perspective view of the sink insert.
Figure 5:
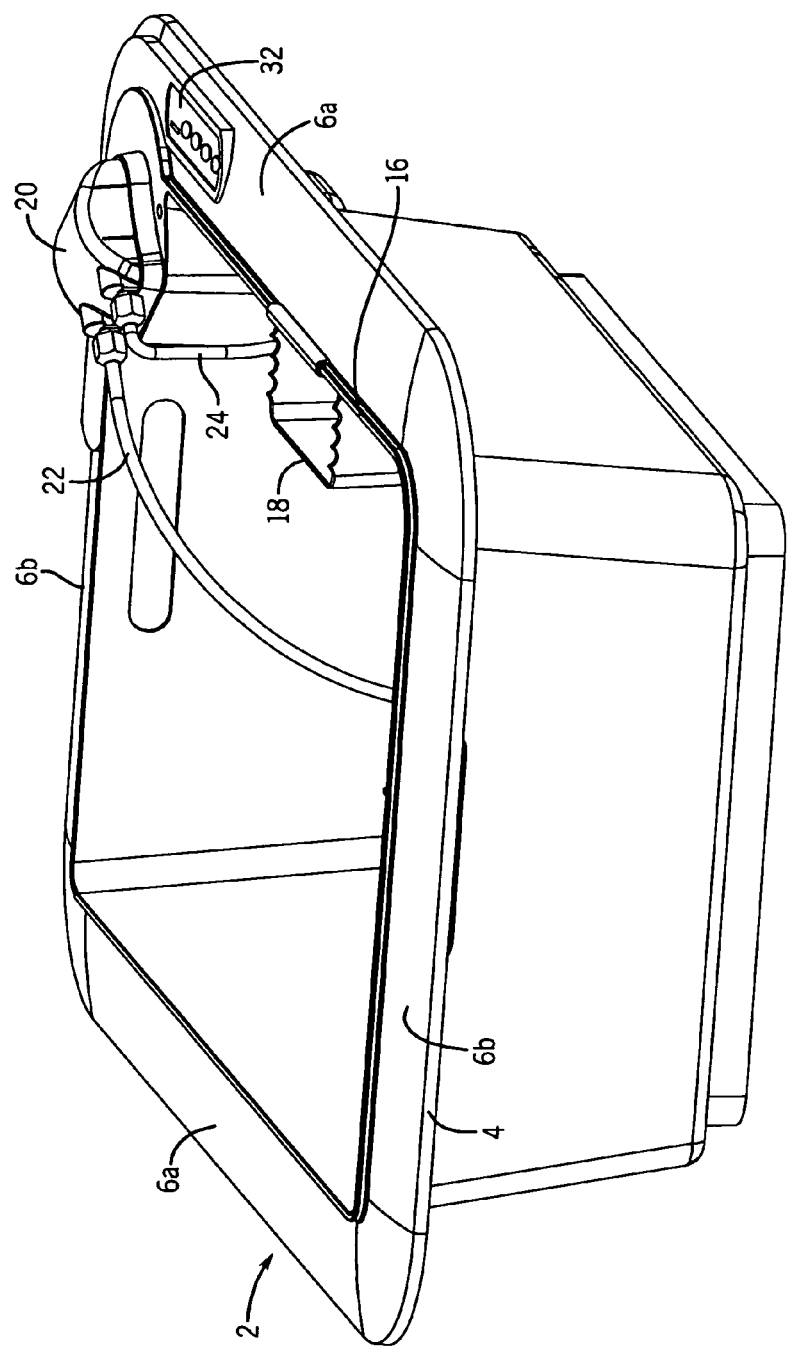
FIG. 5 is a right side perspective view of the sink insert.

The basin side walls 8a, 8b have on their upper ends a plurality of lip formations 6a, 6b that are shaped, sized and adapted to extend over the upper ends of the side walls of a sink 200. The lip formations are best seen in FIGS. 3-5. The lip formations 6a, 6b accordingly are adapted to act as supports that hold the sink insert 2 so that it can rest suspended or hanging above the bottom of the sink 200. The lip formations accordingly are formed and serve as a flange around the top to support the basin while hanging in a sink. The basin flange is ribbed on the underside to provide increased structural strength and rigidity.

The lip formations 6a, 6b can be molded together at their ends to form one continuous lip formation extending around one or more corners of the basin 4. The basin side walls 8b, 8b include cutout portions 12, 12, in the form of apertures that allow overflows of the liquid in the basin to drain into the sink, rather than to flow over areas adjacent thereto, or serve as handles positioned to allow a user to grip and lift the sink insert 2 to move it into and out of the sink 200. The handles 14, 14, depicted in FIG. 7, preferably are formed as an integral grip area having apertures suitable for allowing overflow of the liquid from the overfilled basin into the sink below. The basin has through-hole handles on either side and ribbing is provided on or near the handles.

The basin has a grooved lip running around the top edge to provide a detenting engagement with the sink or other support.

Figure 2:
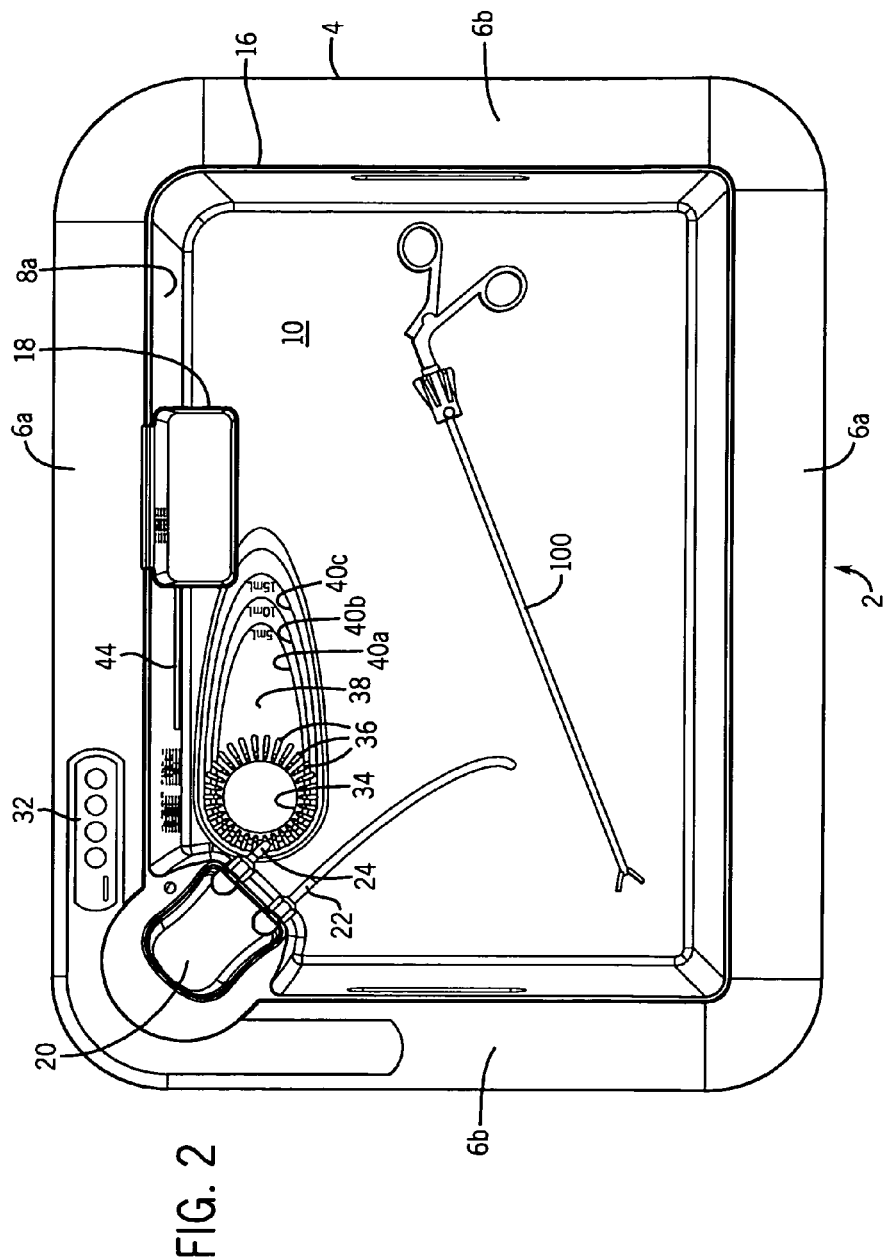
FIG. 2 is a top plan view of the sink insert.
Figure 8A:
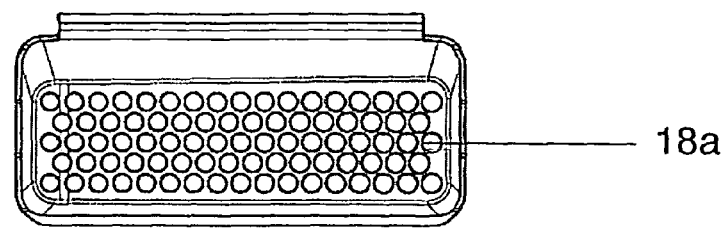
FIG. 8a is a bottom perspective view showing one type of caddy.
Figure 8B:
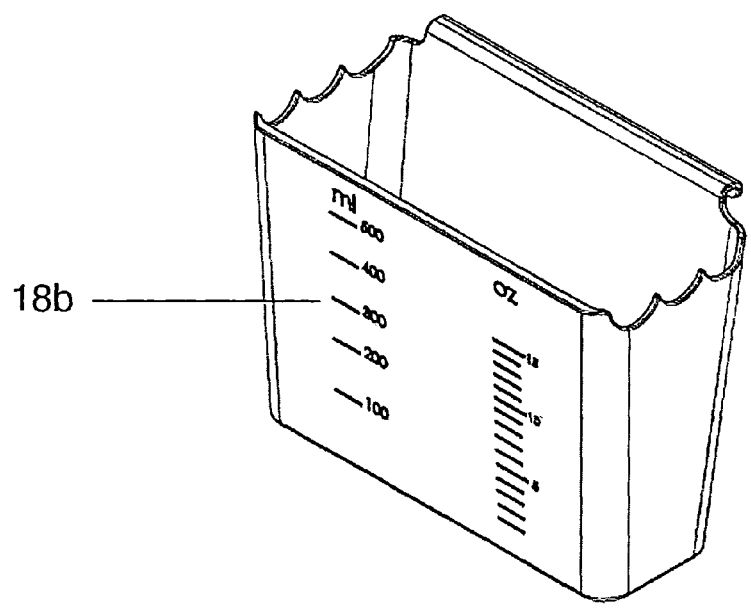
FIG. 8b is a front perspective view showing another type of caddy.

The basin 4 includes a formation in the nature of a rail 16 positioned around one or more of the upper ends of the side walls 8a, 8b of the basin 4. This rail 16, depicted in FIGS. 1 and 2, is formed in the basin 4 for holding items such as hooks for convenient storage of cleaning tools such as brushes, or such as one or more caddies 18 for holding cleaning additives, cleaning implements or medical/surgical items to be cleaned. Examples of the caddies 18 are shown in FIGS. 2, 8a and 8b. The caddy 18 can additionally contain perforations 18a, shown in FIG. 8a, in its bottom and/or side walls to allow drainage and air circulation to dry cleaning implements placed in the caddy 18. Another embodiment of the caddy 18 contains no perforations and contains calibrated measurement markings or fill lines 18b, shown in FIG. 8b, to allow measurement of cleaning additives in the caddy 18. The rail 16 is shaped to slidably engage such caddies 18, hooks, holsters, or other accessories (not shown) suspended from the rail 16 so that the user can optimally position the caddies 18 or hooks, etc. along the side walls, by sliding the caddies 18 or hooks into preferred positions along the rail. Gun-rack or other styles of ridges can be formed in the sink insert at appropriate positions for draining, drying, or storage of brushes or other cleaning tools, as desired by the user.

The form and size of the sink insert 2 is selected based on the intended usage of the sink insert 2. The length and width dimensions are selected to fit standard sized medical laboratory sinks, such as the sink 200 partially depicted in FIG. 7. A shallower sink insert 2 provides for cleaning of smaller items while minimizing bending by the technician and using less water and additive than would be required to fill the sink to an equivalent work level. A deeper sink insert 2 allows for cleaning of larger items while also reducing the total amounts of water and additive required. The insert 2 can optionally be deeper than the sink 200 itself, in which case the bottom of the basin 4 would rest upon the bottom inner surface of the sink and the side walls of the basin 4 would extend upwardly beyond the upper ends of the side walls of the sink, which could raise the working height for a taller technician. By significantly reducing the capacity of the sink 200, the sink insert 2 enables the technician to fill the basin 4 faster and drain it quicker while reducing unnecessary consumption of water and additives, while also allowing for removal of the sink insert 2 to allow large devices to be processed in the deeper sink 200. The form and size are selected so as to allow easy carrying by the technician, and also to allow positioning of the sink insert 2 on a countertop so that the sink insert 2 can alternatively be used as a secondary receptacle to the sink 200.

The material of which the basin 4 is formed is an appropriate synthetic resin, optionally formed upon a base material such as a metal, and/or optionally formulated containing appropriate reinforcement additives and/or plasticizers. The basin is preferably molded out of polypropylene or polyethylene plastic, with a preferred nominal wall thickness of approximately 0.125 inches. Alternatively, an appropriate metal could be selected for the material of the body of the basin. Plastic parts can be formed of polycarbonate plastics, CNC machined. The material of which the basin is formed must possess appropriate properties for the working conditions typical for cleaning of medical/surgical devices. In particular, the material must possess sufficient strength and rigidity to maintain form when carried full of water; sufficient chemical and thermal resistance to withstand repeated contact with typical cleaning solvents and additives and working temperatures; sufficient impact, abrasion, cracking and shatter resistance; flame/fire resistance to satisfy hospital safety standards and regulations; electrical insulation and arcing/sparking resistance to satisfy hospital safety standards and regulations; impermeability, surface hardness, and chemical non-reactivity sufficient to avoid diffusion and absorption of additives into the material of the basin 4; and low weight to assure that a user can carry a sink insert 2 when full of water.

The sink insert includes an integral pump 20, shown in FIGS. 1-2. The pump is provided for flushing the cleaning liquid under pressure into the lumen of the medical/surgical device 100. The pump 20 is an electrically powered pump unit connected to the basin 4 in a manner that protects the pump's electrical and other non-waterproof components from contact with liquid in the basin 4. In this regard, the pump 20 can be inserted into a pump holding receptacle formation 26 molded in the basin, designed to be integral to the basin 4 and yet formed to prevent contact of liquid in the basin 4 or in the sink 200 with pump components, such as electrical components, that must be kept dry. The back wall of the pump holding receptacle 26 is shown in FIG. 4, with the front wall of the pump holding receptacle 26 being cut away in FIG. 4, in order to show the pump motor 28, which is positioned within the receptacle 26. The pump receptacle 26 is formed in a manner that allows removal and replacement of the pump 20 for repair. A waterproof or other protective cap for the motor is provided for protection of the pump from water, moisture or impact.

The pump 20 can be a peristaltic pump or any other form of pump adapted for pumping liquids. The pump 20 includes a pump inlet tube 22, shown in FIG. 1 with its ends cut away to reveal other features. Pump inlet tube 22 is shown in its typical longer length in FIG. 2. Pump inlet tube 22 preferably is a flexible rubber or plastic tube that has its free, open end positioned under the surface of the cleaning liquid in the basin 4, to draw cleaning liquid from the basin 4 into the pump 20 through the pump inlet tube 22. Alternatively, pump inlet tube 22 comprises or is formed of a rigid adaptor extending outwardly from the pump 20 as shown in FIG. 1, having a male or female mating end portion (not shown) that allows for sealed connection to other tubes, or to tubular instruments or adaptors.

The pump 20 includes a pump outlet tube 24, depicted in FIG. 1, shown therein with its ends cut away to reveal other features. Pump outlet tube 24 is shown in its typical longer length in FIG. 2. Pump outlet tube 24 preferably is a flexible rubber or plastic tube that carries the liquid ejected under force from the pump 20 into the lumen of the medical/surgical device 100 to be cleaned. The pump outlet tube 24 thus can include at its end means for sealed attachment to the lumen of the medical device to be cleaned, such as one or more removable male or female adaptors (not shown) designed to enable sealed connection between the end of the pump outlet tube 24 and the lumen, to allow the pumped fluid to be injected under force from the pump 20 through the pump outlet tube 24 into the lumen without significant loss of pressure. Alternatively, the pump outlet tube 24 comprises or is formed of a rigid adaptor extending outwardly from the pump 20 as shown in FIG. 1, having a male or female mating end portion that allows for sealed connection to other tubes, or to tubular instruments or adaptors. In the case of a peristaltic pump, which is known in the art, the inlet tube 22 and the outlet tube 24 can be two ends of the same single continuous piece of elastomeric tubing, with the middle portion of the tubing being threaded into the peristaltic pump, to receive the compression from the rollers or shoes of the peristaltic pump. The basin includes a clip or holder means for optional holding of one or more of the inlet and outlet tubes in position as desired by the user.

The pump 20 includes an electric pump motor 28 (partially shown in a cutaway of the receptacle 26 in FIG. 4), and an electrical power supply 30, partially shown in FIG. 4, which optionally includes an AC electrical cord and/or a battery unit or DC adaptor unit and cord to supply electrical power to operate the pump 20 with optional strain-relief features such as surrounding reinforcements. The pump can be removable, and the sink insert can be adapted to include a through hole or other access for insertion of a power cord of a removable pump. The operation of the pump motor 28 is controlled by use of a pump control panel 32 containing buttons and/or switches that are manually operable by the user, as shown in FIG. 2.

The pump operates in reverse and in pulse mode, preferably configured to provide a pulsating flow as well as a steady flow, either forwardly or backwardly, of the cleaning liquid. The pump 20 has a number of control buttons or switches for operation of the pump 20 in a manner ideal for cleaning of lumens, including variable flow adjustment, pulsating vs. steady flow, and a pump pulse option. The pump pulse option will allow the technician to push a button on the control panel 32 to put the pump into a pulse mode or pulse cycle, wherein the flow in the pump output tube 24 automatically and repeatedly pulses forwardly into the lumen and then reverses backwardly out of the lumen, to push cleaning liquid and/or gases forcefully back and forth into an area in a lumen that may have a clog.

There is a water resistant lip formed around the pump hole formed in the sink insert to receive insertion of the pump to aid in protection of the pump from water. The sink insert includes means for improvement of heat transfer, so that excess heat generated by the pump motor can be radiated to the exterior of the sink insert, the means including features such as heat-sink ribbing.

As shown in FIGS. 1 and 2, in the basin floor there is formed a drain 34 having a removable stopper or plugging mechanism to permit upon opening the flow by gravitational force of the liquid from the basin 4 into the sink 200 or other receptacle below the basin 4. This drain 34 will allow the technician to empty the sink insert 2 without lifting and pouring. The drain 34 includes a catch system for capturing small device parts and preventing their exit from the basin through the drain. In a preferred embodiment, the drain catch system is formed from a plurality of catch protrusions 36, 36, 36 integrally formed in the floor of the basin, and preferably extending upwardly from the floor of the basin and surrounding the drain 34, as shown in detail in FIG. 6. The catch protrusions are shaped, positioned and configured to hold back small cleaning tools, medical devices, or medical device parts, as the liquid drains out of the basin 4 when the drain 34 is opened. Catch protrusions preferably are formed as a plurality of protruding ribs arrayed around the drain hole.

Figure 6:
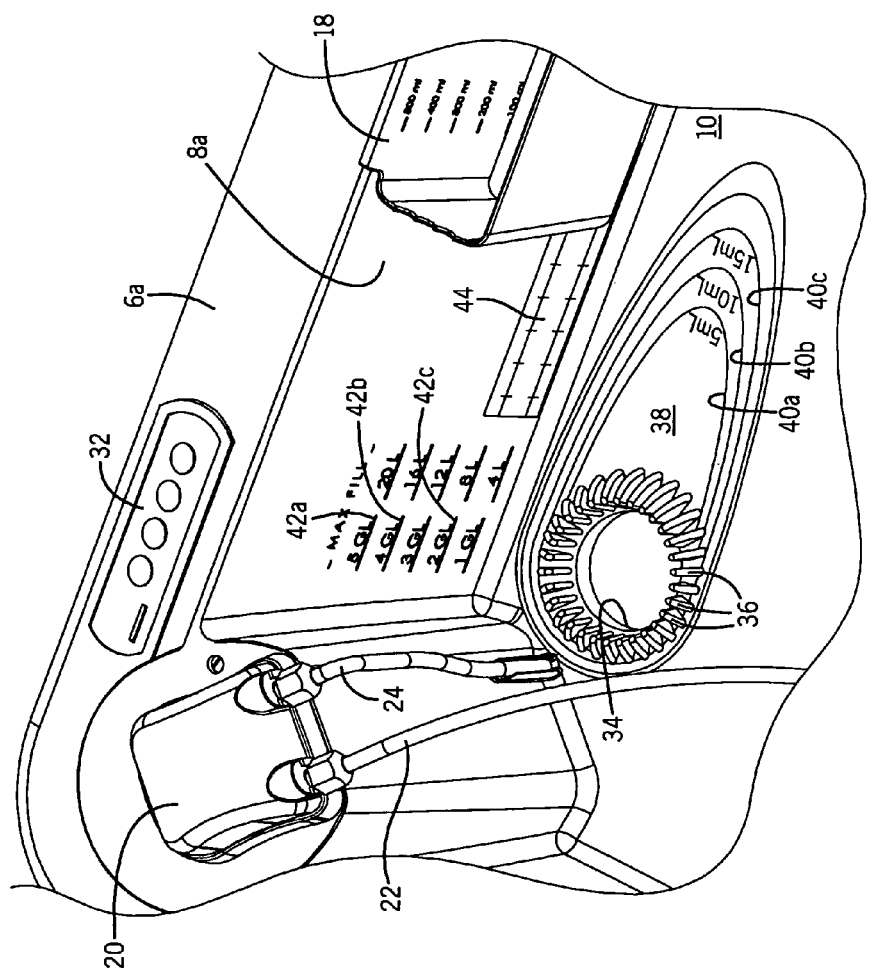
FIG. 6 is a top perspective view of the drain and additive reservoir features of the sink insert, enlarged to show detail.

The basin 4 includes an integrated measurement system designed to provide for accurate measurement of additives and water in order to easily provide for the quick and accurate dilution of additives in water (or other liquid) to prepare the cleaning liquid to be used for cleaning the medical/surgical devices 100. The measurement system includes an additive reservoir 38 positioned in the basin floor 10, shown in FIGS. 1,2 and 6. The additive reservoir 38 typically would be formed as a concave depression integrally formed in the basin floor 10, and formed in any appropriate shape. The reservoir 38 is shown as a roughly ovoid depression surrounding the drain 34 in the basin floor 10 in the drawings, in particular in the detail shown in FIG. 6. The additive reservoir 38 includes a plurality of additive fill lines 40a, 40b, 40c positioned to define particular pre-measured and calibrated liquid volumes applicable when the reservoir is filled with a liquid to a particular fill line 40a, 40b, or 40c. The additive fill lines are shown in FIG. 6. Each additive fill line is marked with a measurement of liquid volume (e.g., 10 mL, 20 mL, 30 mL, and/or 1 oz., 2 oz., 3 oz, etc.) displayed in volume marks showing the amount of additive contained when the reservoir 38 has been filled to that particular fill line. The additive reservoir 38 can be formed in any suitable position in the basin floor 10, but a preferred configuration has the reservoir 38 formed around the drain 34, as shown in FIG. 6.

The additive reservoir optionally can be configured and shaped to receive and measure the additives in solid form, in addition to or as an alternative to receiving the additives in liquid form. The solid additives typically would be in forms such as powder, pellet, or granular forms. The reservoir configured and shaped to receive and measure such additives would include a plurality of additive fill lines 40a, 40b, 40c that are calibrated, shaped, and marked to define pre-measured units of dry volume and/or dry weight measurements.

The integrated measurement system also includes basin fill lines 42a, 42b, 42c formed on one or more of the side walls 8a, 8b of the basin 4, positioned to define a particular pre-measured volume of liquid (typically water, but could alternatively be another liquid or solvent to be used for cleaning the medical/surgical device) applicable when the basin 4 is filled to a particular basin fill line 42a, 42b, or 42c. The basin fill lines are shown in FIGS. 1-2. Each basin fill line is marked with a measurement of liquid volume (e.g., 10 L, 15 L, 20 L and/or 1 gal, 3 gal, 5 gal, etc.) displayed in volume marks showing the amount of water or cleaning fluid contained when the basin 4 has been filled to that fill line. The basin 4 is designed and configured with precise precalibrated measurement of the volumes encompassed within the respective reservoir fill lines 40a, 40b, 40c and basin fill lines 42a, 42b, 42c, to ensure that filling to the applicable reservoir fill line with additive, and filling to the applicable basin fill line with water and/or other solvent liquid, will result in the exact expected level of concentration of the additive that is required in the resulting cleaning liquid to be used on the medical instrument. The number and volume of the additive fill lines and basin fill lines given here and depicted in the figures merely serve as examples; any number of lines could be formed in the basin and any appropriate volume levels could be selected based on the desired size and usage of the sink insert.

The additive fill lines and basin fill lines and the volume marks are applied to the basin in any appropriate way. A preferred configuration has the additive fill lines, basin fill lines, and volume marks integrally formed with the basin 4, as moldings extending outwardly as slight protrusions from the basin surface, as shown in FIGS. 1 and 6. Alternatively, the lines and marks can be affixed to the basin 4 in the form of etched or molded depressions formed in the surface of the basin 4, or applied as adhesive stickers or painted onto the surface of the basin.

The basin includes a thermometer 44, shown in FIG. 1. The thermometer 44 preferably is formed as a liquid crystal strip thermometer affixed to the floor. 10 or a side wall 8a of the basin 4, in a position suitable for viewing the displayed temperature of the water in the basin. The thermometer typically is glued to the side wall but can be affixed in other manners. A position of the thermometer 44 low on the side wall 8a or on the floor 10 of the basin 4 makes assessment of the water temperature possible even when a small amount of water is in the basin 4. The liquid crystal strip thermometer 44 preferably has temperature indicators covering a range of temperatures from approximately 80° F. to approximately 120° F., which represents typical temperatures specified in the use of cleaning liquids including typical additives used to clean the sort of medical/surgical devices 100 in question.

Also contemplated is another version of the sink insert in a compact size, for use in smaller applications, in smaller sinks, as a stand alone unit, or more highly portable unit of lighter weight when empty or full, sized to have a weight low enough to be carried by a user when full of cleaning liquids. This smaller module is preferably molded out of polypropylene or polyethylene plastic with a preferred nominal wall thickness of approximately 0.080 inches. The smaller module has calibrated fill markings molded into it, as in the regular sink insert. Optionally, either the standard sink insert as claimed, or the smaller module, can be molded to have a slanted floor to concentrate small amounts of liquid into a chosen location. The smaller module has a hooked lip with protruding bumps to provide a detenting engagement with the basin.

The invention claimed is:
1. A sink insert for cleaning a medical or surgical device having a lumen, comprising:
a basin, and
an electrically powered pump connected to the basin, wherein the basin is shaped to be inserted into a sink and to hold cleaning liquid, and comprises:

lip portions formed as flanges at upper ends of side walls of the basin and shaped to extend outwardly in lateral directions to overlap upper ends of side walls of the sink;

a drain formed in a floor of the basin for draining of the cleaning liquid;

an additive reservoir integrally formed in the floor of the basin in the form of a depression, comprising additive fill lines defining a plurality of pre-calibrated volume measurement areas for measurement of additives to the cleaning liquid;

basin fill lines positioned on one or more side walls of the basin, defining a plurality of pre-calibrated volume measurement areas for measurement of a liquid filled into the basin to form the cleaning liquid; and a thermometer positioned on one or more of said side walls of the basin for measurement of temperature of the cleaning liquid, and wherein said pump comprises an inlet tube configured for drawing of the cleaning liquid from the basin into the pump, and further comprises an outlet tube configured for pressurized output of the cleaning liquid under pressure supplied by said pump and directed to the medical or surgical device.

2. The sink insert according to claim 1, wherein the pump further comprises means for reversal of pump flow, and the inlet tube is configured for expelling of the cleaning liquid from the pump into the basin under pressure supplied by the pump, and the outlet tube is configured for pressurized drawing of the cleaning liquid under pressure supplied by said pump.

3. The sink insert according to claim 1, further comprising one or more cutout portions in the form of apertures formed in the side walls of the basin, configured to allow overflow of the cleaning liquid in the basin to drain into the sink.

4. The sink insert according to claim 1, further comprising handles formed in the lip portions.

5. The sink insert according to claim 1, further comprising one or more cutout portions in the form of apertures formed in the side walls of the basin, configured to serve as handles positioned to allow a user to grip and lift the sink insert.

6. The sink insert according to claim 1, further comprising a rail affixed to at least one side of the basin, said rail being shaped to slidably engage with and to hold a cleaning tool, a caddy, and/or a hook.

7. The sink insert according to claim 1, wherein the pump is a peristaltic pump and the inlet tube and the outlet tube are two ends of a single continuous piece of elastomeric tubing having its middle portion threaded into the peristaltic pump.

8. The sink insert according to claim 1, further comprising an electrical power supply electrically connected to supply electrical power to the pump, and comprising at least one of an AC electrical cord with an AC electrical adaptor plug, a battery unit, or a DC adaptor unit with an AC electrical adaptor plug and cord.

9. The sink insert according to claim 1, wherein the additive reservoir integrally formed in the floor of the basin surrounds the drain.

10. The sink insert according to claim 1, further comprising a drain catch system comprising a plurality of catch protrusions integrally formed in the floor of the basin, said catch protrusions being formed as ribs protruding upwardly from the floor of the basin and surrounding the drain.

11. The sink insert according to claim 1, wherein the pump is removable.

12. The sink insert according to claim 1, wherein a pump receptacle is formed in the basin, and the pump is removable.

13. A sink insert for cleaning a medical or surgical device having a lumen, comprising:

a basin, and an electrically powered pump connected to the basin, wherein the basin is shaped to be inserted into a sink and to hold cleaning liquid, and comprises:

an additive reservoir integrally formed in a floor of the basin in the form of a depression, comprising additive fill lines defining a plurality of pre-calibrated volume measurement areas for measurement of additives to the cleaning liquid; and basin fill lines positioned on one or more side walls of the basin, defining a plurality of pre-calibrated volume measurement areas for measurement of a liquid filled into the basin to form the cleaning liquid;

and wherein said pump comprises an inlet tube configured for drawing of the cleaning liquid from the basin into the pump, and further comprises an outlet tube configured for pressurized output of the cleaning liquid under pressure supplied by said pump and directed to the medical or surgical device.

14. The sink insert according to claim 13, wherein the pump further comprises means for reversal of pump flow, and the inlet tube is configured for expelling of the cleaning liquid from the pump into the basin under pressure supplied by the pump, and the outlet tube is configured for pressurized drawing of the cleaning liquid under pressure supplied by said pump.

15. The sink insert according to claim 13, further comprising one or more cutout portions in the form of apertures formed in the side walls of the basin, configured to allow overflow of the cleaning liquid in the basin to drain into the sink.

16. The sink insert according to claim 13, further comprising one or more cutout portions in the form of apertures formed in the side walls of the basin, configured to serve as handles positioned to allow a user to grip and lift the sink insert.

17. The sink insert according to claim 13, further comprising lip portions formed as flanges at upper ends of side walls of the basin and shaped to extend outwardly in lateral directions to overlap upper ends of side walls of the sink.

18. The sink insert according to claim 17, further comprising handles formed in the lip portions.

19. The sink insert according to claim 13, further comprising a rail positioned around one or more of upper ends of side walls of the basin.

20. The sink insert according to claim 13, wherein the pump is a peristaltic pump and the inlet tube and the outlet tube are two ends of a single continuous piece of elastomeric tubing having its middle portion threaded into the peristaltic pump.

21. The sink insert according to claim 13, further comprising an electrical power supply electrically connected to supply electrical power to the pump, and comprising at least one of an AC electrical cord with an AC electrical adaptor plug, a battery unit, or a DC adaptor unit with an AC electrical adaptor plug and cord.

22. The sink insert according to claim 13, further comprising a drain formed in the floor of the basin for draining of the cleaning liquid.

23. The sink insert according to claim 22, wherein the additive reservoir integrally formed in the floor of the basin surrounds the drain.

24. The sink insert according to claim 22, further comprising a drain catch system comprising a plurality of catch protrusions integrally formed in the floor of the basin, said catch protrusions being formed as ribs protruding upwardly from the floor of the basin and surrounding the drain.

25. The sink insert according to claim 13, further comprising a thermometer positioned on one or more of said side walls of the basin for measurement of temperature of the cleaning liquid.

26. The sink insert according to claim 13, wherein the pump is removable.

27. The sink insert according to claim 13, wherein a pump receptacle is formed in the basin, and the pump is removable.

* * * * *